(12) United States Patent
Gering

(10) Patent No.: US 9,730,671 B2
(45) Date of Patent: Aug. 15, 2017

(54) SYSTEM AND METHOD OF VOICE ACTIVATED IMAGE SEGMENTATION

(71) Applicant: David Thomas Gering, Waunakee, WI (US)

(72) Inventor: David Thomas Gering, Waunakee, WI (US)

( * ) Notice: Subject to any disclaimer, the term of this patent is extended or adjusted under 35 U.S.C. 154(b) by 0 days.

(21) Appl. No.: 14/874,425

(22) Filed: Oct. 3, 2015

(65) Prior Publication Data
US 2016/0104293 A1 Apr. 14, 2016

Related U.S. Application Data

(60) Provisional application No. 62/071,897, filed on Oct. 3, 2014.

(51) Int. Cl.
| | |
|---|---|
| A61B 8/00 | (2006.01) |
| A61B 8/08 | (2006.01) |
| A61B 6/00 | (2006.01) |
| A61B 6/03 | (2006.01) |
| G01R 33/54 | (2006.01) |
| G06F 3/16 | (2006.01) |
| G06T 11/00 | (2006.01) |

(52) U.S. Cl.
CPC ............ *A61B 8/085* (2013.01); *G01R 33/546* (2013.01); *G06F 3/167* (2013.01); *G06T 11/001* (2013.01); *A61B 6/032* (2013.01); *A61B 6/037* (2013.01); *A61B 6/461* (2013.01); *A61B 6/468* (2013.01); *A61B 8/00* (2013.01)

(58) Field of Classification Search
None
See application file for complete search history.

(56) References Cited

U.S. PATENT DOCUMENTS

| | | | | |
|---|---|---|---|---|
| 5,600,765 | A * | 2/1997 | Ando | G06F 3/038 345/668 |
| 2004/0189720 | A1* | 9/2004 | Wilson | G06K 9/00355 715/863 |
| 2007/0133852 | A1* | 6/2007 | Collins | A61B 8/08 382/128 |
| 2011/0317888 | A1* | 12/2011 | Simon | G06K 9/6207 382/128 |
| 2014/0033045 | A1* | 1/2014 | Kshirsagar | G06F 3/167 715/728 |
| 2014/0058584 | A1* | 2/2014 | Weng | G06F 7/00 701/1 |

(Continued)

OTHER PUBLICATIONS

R. Bolt, "Put-That-There: Voice and Gesture at the Graphics Interface," Computer Graphics, vol. 14, No. 3, 1980, pp. 262-270.*

(Continued)

*Primary Examiner* — Matthew Bella
*Assistant Examiner* — Soo Shin

(57) ABSTRACT

A method and system for incorporating voice commands into the interactive process of image segmentation. Interactive image segmentation involves a user pointing at an image; voice commands quicken this interaction by indicating the purpose and function of the pointing. Voice commands control the governing parameters of the segmentation algorithm. Voice commands guide the system to learn from the user's actions, and from the user's manual edits of the results from automatic segmentation.

20 Claims, 3 Drawing Sheets

(56) References Cited

U.S. PATENT DOCUMENTS

| | | | |
|---|---|---|---|
| 2014/0094679 A1* | 4/2014 | Kovacs | G06T 7/136 600/407 |
| 2014/0244072 A1* | 8/2014 | Vaghefinazari | G01C 21/3608 701/2 |
| 2014/0371955 A1* | 12/2014 | Vaghefinazari | G01C 21/3608 701/2 |
| 2015/0142437 A1* | 5/2015 | Kobayashi | G06F 3/167 704/246 |
| 2016/0225192 A1* | 8/2016 | Jones | G06F 3/012 |

OTHER PUBLICATIONS

A. Hakata et al., "Object identification by language in a user interface using language and image information," SIGCHI Jan. 1990, vol. 21, No. 3, pp. 33-36.*

* cited by examiner

SYSTEM AND METHOD OF VOICE ACTIVATED IMAGE SEGMENTATION

CROSS-REFERENCE TO RELATED APPLICATIONS

The present invention relates to the U.S. provisional patent application with an identical title, application No. 62/071,897 and filing date of Oct. 3, 2014.

STATEMENT REGARDING FEDERALLY SPONSORED RESEARCH OR DEVELOPMENT

Non-applicable.

REFERENCE TO SEQUENCE LISTING, A TABLE, OR A COMPUTER PROGRAM LISTING COMPACT DISC APPENDIX

Non-applicable.

BACKGROUND OF THE INVENTION

The present invention relates generally to image segmentation, or the process of assigning labels to the elements in an image. More specifically, it relates to semi-automatic 3D medical image segmentation, where there is an interactive process for labeling each voxel according to tissue type represented.

Image segmentation has been an active area of research in the computer vision community, and the medical image analysis community. The ultimate goal is often a fully automatic algorithm that need not require input from a human user. In practical applications, however, stringent goals for accuracy may compel assistance from an expert. Semi-automatic algorithms may query the user for seed points to initiate region growing, or training points to initialize probability distributions (used by Bayesian or kNN classification), or threshold levels to govern expansion terms of level set methods, or strokes of a virtual paint brush to indicate foreground and background objects (used by level set or GrowCut algorithms), or bounding boxes to encapsulate regions of interest to provide spatial constraints. Furthermore, they may allow interactive edits of automatically-computed results by relocating control points of active contours, or by manipulating tools for repositioning contours. It may behoove the user to manually redraw an incorrect border astride the perimeter of a structure. Fully manual segmentation involves a person drawing all the boundaries of all structures, but such tedious monotony is prone to error and inter-observer variability. Any method less than nearly fully automatic could be prohibitively expensive to deploy in clinical settings due to how much time is consumed by healthcare personnel. The user interface device is usually a computer mouse, stylus, or touch screen, but could be a trackball, haptic interface, or eye-gaze detector in academic settings.

Segmented images are essential for various clinical applications that stand to benefit from the presence of images where each relevant anatomic structure has been delineated. Segmentation can be a valuable ally in treating cancer, whether by radiotherapy, chemotherapy or surgical resection. Image guided radiation therapy (IGRT) uses cross-sectional images of the patient's internal anatomy to better target the radiation dose to the tumor while sparing exposure of healthy organs. The radiation dose delivered is controlled with intensity modulated radiation therapy (IMRT), which involves changing the size, shape, and intensity of the radiation beam to conform to the size, shape, and location of the patient's tumor. IGRT and IMRT simultaneously improve control of the tumor while reducing the potential for acute side effects due to irradiation of healthy tissue surrounding the tumor. Segmentation is widely employed for IGRT and IMRT because the process of planning the delivery is a quantitative and numerical exercise best suited for a computer. Chemotherapy, in contrast to radiotherapy, tends to follow a more qualitative planning process whereby the tumor's response to the treatment regimen is visually monitored, such as by a CT scan every couple months. Precise quantification of tumor extent would be useful for decision making, but oncologists are too short on time to be guiding semi-automatic segmentation methods, and they're unlikely to be trained in using expensive analysis workstations. Surgical resections and biopsies benefit from image segmentation by rendering 3D views of the spatial relationships between organs for surgical planning and guidance. Beyond treating cancer, image segmentation is utilized in longitudinal studies that track quantitative measurements such as anatomic dimensions, cross-sectional areas, or volumes.

Recent improvements in speed, accuracy, and automation of segmentation algorithms have nearly obviated human intervention in certain research applications. These applications tend to focus on tissue that appears normal, such as quantitative measurements of neuroanatomy. Disease can vary in unexpected ways that are complicated to model, and disease often presents special cases and outliers that extend beyond the understanding of computer software. What the software needs is interaction with a keen physician, quick and clever, to astutely manipulate facts.

Even if fully automatic algorithms could become sufficiently accurate for routine clinical use, certain physicians vary in personal approach and requirements, so algorithms would still benefit from some manner of catering to individual preferences. When the full knowledge and artful discernment of the physician(s) is reflected in the output of the segmentation, then the downstream processes to which segmentation is an input can become effectual instruments.

The foregoing discussion highlights the need for new semi-automatic strategies that can incorporate the expertise of the physician(s) into the segmentation process. The key enabler is to employ their penetrating intellect with a minimum of time and expense. The present invention proposes voice-activation as this key enabler. Voice recognition has a history of employment by the medical profession for dictation and medical transcription. Healthcare researchers have also experimented with voice-activated image retrieval, operating an imaging scanner by voice commands, and hands-free manipulation of a display of 3-D angiography by a surgeon in the operating theater.

BRIEF SUMMARY OF THE INVENTION

A method for voice activated image segmentation is introduced, which allows the physician to quickly and easily interact with the computerized segmentation process, thereby imparting his/her skilled expertise to the segmented result.

In some embodiments, the system is equipped to automatically respond to voice commands, such as "Grow more anteriorly toward ventricle," because it segments not only the "target" structures, but also the "situational" structures, or surrounding anatomy, to which the physician may refer. Both target and situational structures are identified in the initial automatic segmentation, which is subsequently presented to the physician for feedback. If the accuracy is deemed sufficient, then no interaction occurs, aside from the physician pronouncing, "It's good." Otherwise, the physician indicates which changes to make, and ideally, these changes are made in real-time, but if processing power is an issue, then the updates could be coarse during interaction, but refined to full resolution after conversation concludes.

In some embodiments, the physician's feedback need not be given by voice alone, but also by "pointing", such as via touch screen or directional eye gaze. For example, the physician may dictate, "Remove this", while pointing to an island of segmentation labels to be erased. The physician could speak, "Add", or, "Grow", if the pointer were being used to add more image elements to the segmented structure. In this manner, the pointer's function is changed from a virtual brush to a virtual eraser without the need for the user to click on a menu, or press a button. Such actions are a great distraction to the user during the interaction, and prolong the segmentation process. The interaction time can be greatly reduced by using voice commands to indicate the pointer's purpose and function, thereby avoiding interruptions.

In some embodiments, the system is a cloud-based solution where intense processing occurs in a high-performance computing environment while the physician interacts with it elsewhere on a mobile device.

In some embodiments, the physician's sequence of interactions is recorded in the form of an annotated video that a human segmenter can watch in case the physician indicates that the computer misunderstood his/her instruction. Thus, the "cloud" could be a system comprising computer servers and a team of humans working in tandem to satisfy physicians positioned at many hospitals around the globe. When the cloud is unsure of something, it can present questions to the physician in the form of annotations on the original automatic segmentation, such as "Is this lesion or cyst?" The physician would answer by "pointing" to the labeled region and answering, "Lesion." For truly complicated cases, the interaction between physician and cloud can take the form of real-time video chat, where the device screen shows the image, as well as annotations marking any pointing/drawing activity, as well as the faces of the physician and segmenter overlaid in small "bubbles" on the perimeter so they can speak with one another clearly.

DETAILED DESCRIPTION OF THE INVENTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

Figure 1:
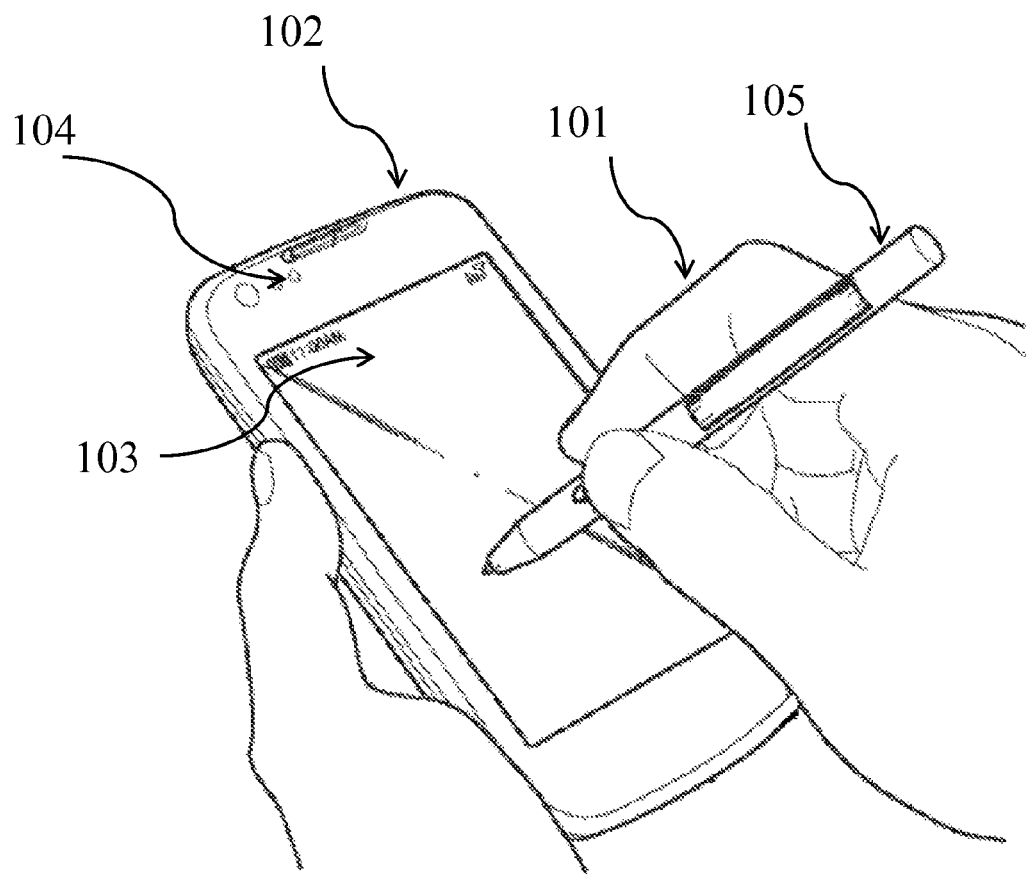
FIG. 1 illustrates a system diagram of an embodiment of the present invention where the pointing device is a stylus.

FIG. 1 is a system diagram of an embodiment where the user 101 interacts with the segmentation process using a voice-activated segmentation system, the system comprising a processing computer 102, an image display 103, a microphone 104, and a pointing device 105. The computer 102 could be a smart phone, tablet, laptop, or desktop computer. The act of pointing at image elements can take many forms; it can be the click of a mouse or trackball; it can be the touch of a finger or stylus on a touchscreen; it can be a gesture toward a very large display; it can be the point toward which the eyes are gazing when eye-tracking is available on the device (such as a camera with real-time computer vision algorithms). In the preferred embodiment, the pointing device is a stylus because interacting with an image feels most natural when the user feels like he/she is drawing directly on the screen that displays the image.

Figure 2:
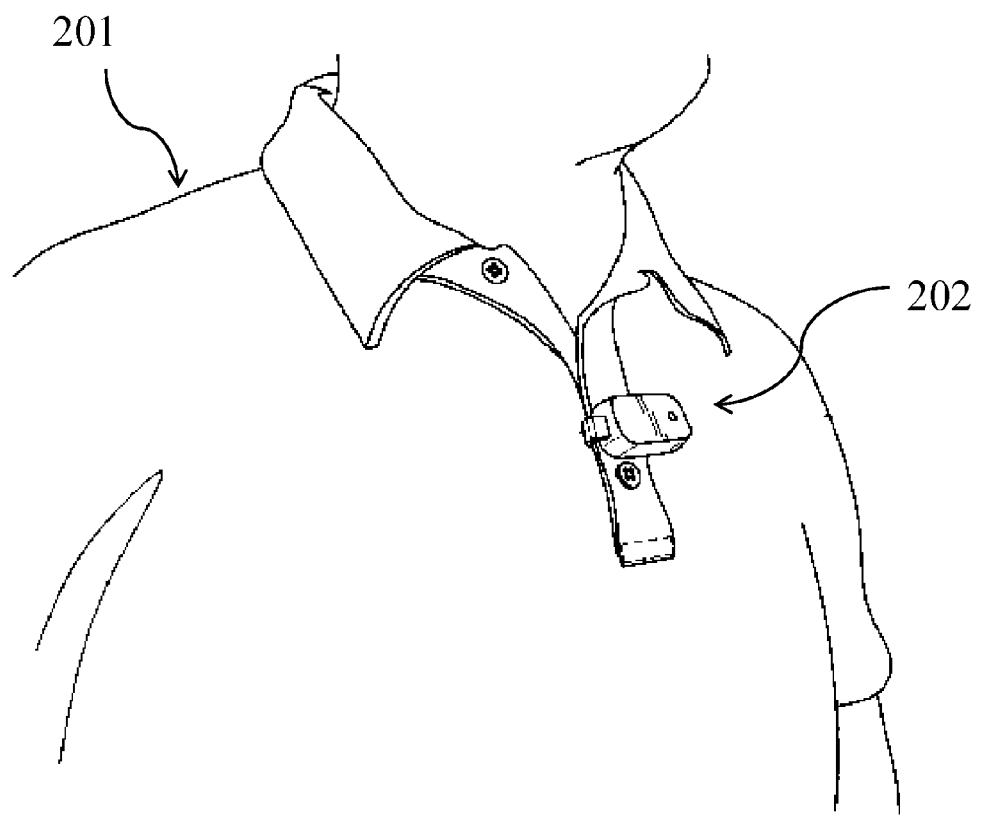
FIG. 2 illustrates a system diagram of a preferred embodiment of the present invention where the user wears a clip-on microphone.

FIG. 2 extends the system diagram of FIG. 1 to add another component, which is for the user 201 to wear a clip-on microphone 202. By placing a microphone close to the mouth, the user is able to talk in quieter tones, so as to not be a distraction to others nearby. In a preferred embodiment, the wearable microphone 202 is in addition to another microphone, referred to as the "background mic". The background mic could be located on the computer 102 (as shown as 104) or the stylus 105, or worn on the back of the user, such as on a headset. While the microphone nearest the mouth records the users spoken words, the background mic collects ambient noise and uses that information for noise cancellation. In this manner, the user could be segmenting in a crowded noisy room without the segmentation system becoming confused by background noise.

Figure 3:
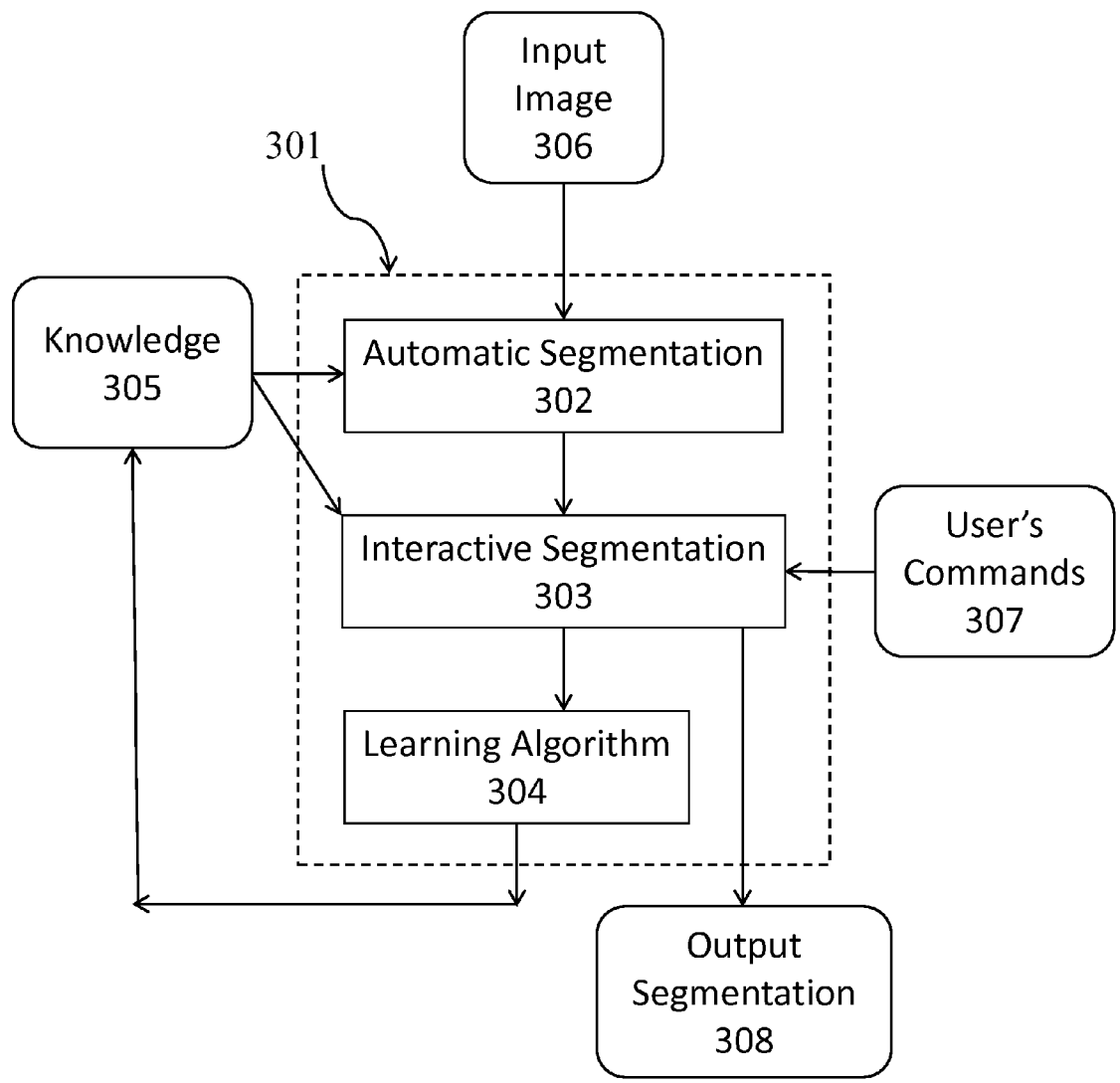
FIG. 3 is a block diagram of a method according to a preferred embodiment of the present invention.

FIG. 3 depicts a block diagram of the method for the preferred embodiment of the invention. The processing system 301 computes an initial segmentation 302 automatically, and shows it to the physician. The physician comments on the results by speaking and pointing to offer commands 307. The device shows its understanding by highlighting the object to which the point was directed, and displaying its interpretation of what was spoken as text. The physician and computer interact until the segmentation is complete 308. The learning algorithm 304 analyzes the editing operations that the physician made during the interaction, and uses this information to update the a priori knowledge 305 used to perform the automatic segmentation 302. Therefore, the system learns from earlier interactions to become smarter for future interactions.

The precise form of the learning algorithm 304 depends on the type of segmentation algorithm 302. For example, if the segmentation algorithm is based on Bayesian classification, then the knowledge 305 consists of prior probability distributions and spatially varying priors. These were initially computed from training data, and each new image that is processed can be added to this training set in order to update the probability distributions. As another example, if the segmentation algorithm 302 is based on statistical shape models, then the probability distributions governing those models (such as curvature, smoothness, angular measures, and radii) may be updated with each successfully completed segmentation. As another example, the distance of the target object from surrounding anatomical landmarks can be extremely helpful to a segmentation algorithm. The difference between the initial distances, and the distances following the user's edits can be noted for the future.

In some embodiments, the ability of the system to learn from the user's past edits is fully automatic, and tailored to the chosen segmentation method. In some embodiments, the learning responds to voice command. For example, a patient could be an outlier, in that there is some exceptional anatomy that the physician wishes to segment without impacting the learning process. The physician would indicate "Don't learn this" or "Exclude this patient."

In some embodiments, vocal commands can be used not only to direct the segmentation, but also to view the results. Segmentations of medical images are often presented as 2D cross-sectional slices and 3D surface renderings side-by-side. Navigating the 2D display involves selecting the orientation of the slices (e.g.: axial, coronal, sagittal), scrolling through the slices along this direction, and zooming and panning within a slice. Navigating a 3D display involves rotating, zooming, panning, and changing the opacity and visibility of occluding structures. It also involves enlarging the 2-D or 3-D views, meaning altering the layout of where things are displayed on the screen. These navigational commands can be given by spoken word in a manner more intuitive than using a mouse. For example, the user can change the slice by saying, "Next slice" or "Previous slice". The user can quickly advance through slices by chaining commands, such as "Next . . . next . . . next . . . next . . . go back . . . back again, stop." Likewise, the user could rotate the viewpoint of a 3-D rendering by saying "Rotate left, more, more, a little more." In situations such as this, the word "more" can be interpreted to mean a typical increment, such as 10 degrees. Then "a little more" would be half the usual increment, or 5 degrees. The user can program the system by directly defining the meaning of commands, "When I say 'Rotate', move 10 degrees."

In those embodiments that include a pointing device, vocal commands serve to alter the pointing mode. This means that the same pointing motion, such as touching an object, will have a different effect depending on what the user says as the user points. For example, to add more image elements (2D pixels or 3D voxels) to a segmented tumor object, the user would say "Add" while clicking on objects, and to erase them, the user would say "Remove" or "Erase" or "Delete". Short one-word commands chosen from a limited vocabulary will be easier for a voice-recognition system to understand correctly. For example, a type of region-growing for liver lesions can be initialized or edited simply by the user pointing at each lesion while saying either "Lesion." or "Not lesion." As another example of simplified vocabulary, the GrowCut algorithm takes input from the user in the form of brush strokes on the foreground and background objects. The user can provide these inputs with seamless hand motion by drawing with the pointer while speaking the name of the object being touched, which is either "Background", or "Foreground."

In addition to altering the mode of the pointer, vocal commands can alter the form of the pointer. Suppose the pointer is being used as a digital paintbrush, then the user can change the radius of the brush by saying "enlarge brush" or "shrink brush". Some edits of segmentation are precise manual drawing, in which the user would say, "Precisely this", while other edits are rough guidelines that the user wants the computer to use as a starting point for finding the boundary from there (based on image intensities and anatomical models), so the user might say, "Roughly this" while drawing that edit.

In some embodiments, voice commands control the governing parameters of the segmentation process. For example, level set methods use curvature for regularization, and the user can dictate "Smaller curvature" or "Larger curvature . . . larger . . . larger . . . good."

The automatic segmentation 302 of anatomic landmarks can be leveraged to make it possible for the user to reference anatomy in the spoken commands. For example, while interacting with a level set or region-growing algorithm, the user may notice that the segmentation "leaked" out of the desired organ into a nearby organ (imagine the liver leaking out between the ribs). The user would say "Avoid ribs", and the computer would then construct an avoidance mask, or region into which the segmentation is not allowed to leak, and then re-apply the region-growing algorithm with this constraint in place. By "mask", we refer to an image that represents a binary segmentation, 1's for foreground and 0's for background. A preferred embodiment allows the user to vocally construct these anatomical masks by saying the names of the organs to include in the mask, and also saying how to employ the mask. For example, the command "Stay below the hyoid", would result in the computer constructing an avoidance mask by first copying the binary segmentation of the hyoid bone onto a blank image, and then filling in all voxels above (superior to) the hyoid. The user could continue to add other organs and directions, such as "And stay left of sternum."

Some embodiments are cloud-based. Some "clouds" could actually be human technicians ready to respond to physicians. As the physician interacts with the segmentation algorithm, a video can be generated automatically that shows all the pointing and drawing strokes that the physician is making on the image. The physician's voice is superimposed over these actions. Given such a video, a human technician or medical resident could perform some meticulous and time-consuming manual image segmentation tasks in response to just a few seconds of a physician's instructions via video. This can be a significant time-saver for the practicing clinician.

The video communication can also go the opposite direction, from cloud to physician. In this case, the cloud, whether a human technician, or automatic algorithm, or some combination thereof, would record a video including voice that requests clarification from the physician. For example, while pointing at a certain object, the video could ask "Is this lesion?", or "I'm unsure about this." The physician can then respond very quickly with a video message that combines voice recording with annotated images to say, for example, "Lesion" or "Edema". Note that this is also a form of system learning, even when the system comprises human technicians, because the technicians are learning to become better segmenters from their interactions with the physicians.

The invention claimed is:

1. A computerized method for image segmentation, the computerized method comprising:
 a) accessing a set of images to be segmented;
 b) initiating an interactive segmentation process on the set of images;
 c) receiving simultaneous voice commands and pointing gestures, wherein the pointing gestures are in combination with the voice commands and wherein the pointing gestures select a region of a segmented structure; and
 d) incorporating the simultaneous voice commands and pointing gestures into the interactive segmentation process to edit segmentation.

2. The computerized method of claim 1, wherein the set of images further comprises one or more MRI image, CT image, PET image, X-ray image, or ultrasound image.

3. The computerized method of claim 2, wherein the interactive segmentation process delineates the boundary of one or more tumor, lesion, nodule, or organs at risk.

4. The computerized method of claim 1, wherein the pointing gestures drag across a region of the set of images, while the simultaneous voice commands specify a segmentation label, and the combination between the voice commands and the pointing gestures results in the interactive segmentation process beginning to segment a new structure with specified label, positioned relative to the pointing gestures.

5. The computerized method of claim 1, wherein the pointing gestures select a segmented structure, while the simultaneous voice commands indicate removal, and the combination between the voice commands and the pointing gestures results in the interactive segmentation process removing the selected segmented structure.

6. The computerized method of claim 1, wherein the pointing gestures select a segmented structure to edit, while the simultaneous voice commands indicate a label, and the combination between the voice commands and the pointing gestures results in the interactive segmentation process changing the label of the selected segmented structure.

7. The computerized method of claim 1, wherein the pointing gestures select a region of a segmented structure to edit and drag in a direction across the set of images, while the simultaneous voice commands indicate addition, and the combination between the voice commands and the pointing gestures results in the interactive segmentation process adding more image elements to the segmented structure in the region selected by the pointing gestures, and oriented along a direction specified by the pointing gestures.

8. The computerized method of claim 1, wherein the pointing gestures select a region of a segmented structure to edit and drag in a direction across the set of images, while the simultaneous voice commands indicate subtraction, and the combination between the voice commands and the pointing gestures results in the interactive segmentation process subtracting image elements from the segmented structure in the reaion selected by the pointing gestures, and oriented along the direction specified by the pointing gestures.

9. The computerized method of claim 1, wherein the pointing gestures select a region of the boundary a segmented structures, while the simultaneous voice commands indicate more or less smoothness, and the combination between the voice commands and the pointing gestures results in the interactive segmentation process editing the segmented structure so that its boundary is more or less smooth in the region selected by the pointing gestures.

10. The computerized method of claim 1, wherein the interactive seamentation process shows its understanding of the simultaneous voice commands and pointing gestures by highlighting an object selected by the pointing gestures while displaying an interpretation of what was spoken as text.

11. The computerized method of claim 1, wherein the pointing gestures select a segmented structure, while the simultaneous voice commands indicate a question, and the combination between the voice commands and the pointing gestures results in the interactive segmentation process recording the question along with the selected segmented structure to which the question refers.

12. The computerized method of claim 11, wherein the recorded question and selected structure are displayed to a user for answering, and an answer is recorded.

13. The computerized method of claim 12 wherein the answer is displayed to a user who continues the interactive segmentation process.

14. The computerized method of claim 12, wherein a user is positioned remotely.

15. A system for voice-activated interactive image segmentation, the system comprising:
 a graphical user interface configured to display images;
 a pointing device;
 at least one microphone; and
 a computer coupled to the graphical user interface, pointing device, and one or more microphones, the computer configured to
 a) access an image dataset;
 b) detect and recognize voice commands;
 c) initiate an interactive segmentation process on the image dataset;
 d) combine voice commands with simultaneous pointing gestures from the pointing device to form combined commands, wherein the pointing gestures select a region of a segmented structure; and
 e) incorporate the combined commands into the interactive segmentation process to edit segmentation.

16. The system of claim 15, wherein the pointing device is selected from the group comprising a computer mouse, stylus, trackball, touch screen, and haptic interface.

17. The system of claim 15, the system further comprising as least one camera, wherein the computer is further configured to
 a) process video from at least one camera in order to detect eye gaze;
 b) combine voice commands with simultaneous eye gaze to form combined segmentation commands; and
 c) incorporate the combined segmentation commands into the interactive segmentation process.

18. A computerized method for image segmentation, the computerized method comprising:
 a) accessing a medical image dataset to be segmented;
 b) applying an automatic segmentation process on the medical image dataset to identify anatomy surrounding a target structure;
 c) initiating an interactive segmentation process on the medical image dataset;
 d) receiving simultaneous voice commands and pointing gestures, the pointing gestures are in combination with the voice commands and wherein the pointing gestures select a region of a segmented structure;
 e) incorporating the simultaneous voice commands and pointing gestures that are coordinated into the interactive segmentation process to edit segmentation; and
 f) storing knowledge gained from the interactive segmentation process for future use by the automatic segmentation process.

19. The computerized method of claim 18, wherein the automatic segmentation process further comprises applying knowledge in the form of one or more of probability distributions, statistical models, spatially varying priors for Bayesian classification, distance transforms, warp fields, shape parameters, spatial relationships to other structures, curvature of boundaries, physiological angles, physiological distances, polynomial coefficients, or profiles along rays emanating from the boundaries of segmented structures.

20. The computerized method of claim 18, wherein the pointing gestures select a segmented structure, while the simultaneous voice commands specify not to learn, and the coordination between the voice commands and the pointing gestures results in the edits of the selected structure not contributing to the learning process.

* * * * *